(12) United States Patent
Rockrohr

(10) Patent No.: US 8,403,892 B2
(45) Date of Patent: Mar. 26, 2013

(54) CONSTRICTING MECHANISM FOR USE WITH A SURGICAL ACCESS ASSEMBLY

(75) Inventor: Brian Rockrohr, Waterbury, CT (US)

(73) Assignee: Covidien LP, Mansfield, MA (US)

(*) Notice: Subject to any disclaimer, the term of this patent is extended or adjusted under 35 U.S.C. 154(b) by 274 days.

(21) Appl. No.: 12/898,030

(22) Filed: Oct. 5, 2010

(65) Prior Publication Data

US 2011/0021876 A1 Jan. 27, 2011

Related U.S. Application Data

(63) Continuation of application No. 12/486,164, filed on Jun. 17, 2009, now Pat. No. 7,914,491.

(60) Provisional application No. 61/081,483, filed on Jul. 17, 2008.

(51) Int. Cl.
*A61M 5/178* (2006.01)

(52) U.S. Cl. ......... 604/167.06; 604/167.03; 604/165.02; 604/164.01

(58) Field of Classification Search .............. 604/164.01, 604/164.02, 164.06, 164.07, 164.09, 164.1, 604/164.11, 164.12, 165.01, 165.02, 167.01, 604/167.02, 167.03, 167.04, 167.06; 606/108, 606/185; 215/212; 251/251, 212; 454/29; 138/45

See application file for complete search history.

(56) References Cited

U.S. PATENT DOCUMENTS

| | | | |
|---|---|---|---|
| 4,094,492 A * | 6/1978 | Beeman et al. ............... 251/212 |
| 4,917,668 A | 4/1990 | Haindl | |
| 5,104,383 A | 4/1992 | Shichman | |
| 5,127,626 A | 7/1992 | Hilal et al. | |
| 5,180,373 A | 1/1993 | Green et al. | |
| 5,197,955 A | 3/1993 | Stephens et al. | |
| 5,209,736 A | 5/1993 | Stephens et al. | |
| 5,209,737 A | 5/1993 | Ritchart | |
| 5,242,412 A | 9/1993 | Blake, III | |
| 5,304,143 A | 4/1994 | Green et al. | |
| 5,308,336 A | 5/1994 | Hart et al. | |
| 5,342,315 A | 8/1994 | Rowe et al. | |
| 5,350,364 A | 9/1994 | Stephens et al. | |
| 5,354,280 A | 10/1994 | Haber et al. | |
| 5,380,288 A | 1/1995 | Hart et al. | |
| 5,388,553 A | 2/1995 | Burke et al. | |
| 5,391,153 A | 2/1995 | Haber et al. | |
| 5,391,154 A | 2/1995 | Young | |
| 5,407,433 A | 4/1995 | Loomas | |
| 5,411,483 A | 5/1995 | Loomas et al. | |
| 5,443,452 A | 8/1995 | Hart et al. | |
| 5,485,553 A | 1/1996 | Kovalick et al. | |

(Continued)

FOREIGN PATENT DOCUMENTS

| EP | 1994896 A1 | 11/2008 |
|---|---|---|
| WO | WO95/07056 A2 | 3/1995 |

(Continued)

OTHER PUBLICATIONS

European Search Report for corresponding EP09251821 date of mailing is Feb. 24, 2012 (3 pgs).

*Primary Examiner* — Nicholas Lucchesi
*Assistant Examiner* — Jenna Zhang

(57) ABSTRACT

The present disclosure relates to a surgical access member for establishing percutaneous access to a surgical worksite within tissue. The surgical access member includes a constricting mechanism that is adapted to removably receive a surgical instrument and resiliently transition between an open state and a constricted state. In the open state, insertion of the surgical instrument through the constricting mechanism is substantially uninhibited. In the constricted state, the constricting mechanism substantially limits transverse movement of the surgical instrument, and may facilitate the creation of a substantially fluid-tight seal therewith.

16 Claims, 13 Drawing Sheets

U.S. PATENT DOCUMENTS

| | | | |
|---|---|---|---|
| 5,492,304 | A | 2/1996 | Smith et al. |
| 5,496,280 | A | 3/1996 | Vandenbroek et al. |
| 5,542,931 | A | 8/1996 | Gravener et al. |
| 5,545,142 | A | 8/1996 | Stephens et al. |
| 5,549,565 | A | 8/1996 | Ryan et al. |
| 5,584,850 | A | 12/1996 | Hart et al. |
| 5,603,702 | A | 2/1997 | Smith et al. |
| 5,628,732 | A | 5/1997 | Antoon, Jr. et al. |
| 5,634,908 | A | 6/1997 | Loomas |
| 5,693,031 | A | 12/1997 | Ryan et al. |
| 5,709,664 | A | 1/1998 | Vandenbroek et al. |
| 5,752,938 | A | 5/1998 | Flatland et al. |
| 5,782,812 | A | 7/1998 | Hart et al. |
| 5,792,113 | A | 8/1998 | Kramer et al. |
| 5,803,919 | A | 9/1998 | Hart et al. |
| 5,820,600 | A | 10/1998 | Carlson et al. |
| 5,827,228 | A | 10/1998 | Rowe |
| 5,871,471 | A | 2/1999 | Ryan et al. |
| 5,895,377 | A | 4/1999 | Smith et al. |
| 6,083,203 | A | 7/2000 | Yoon |
| 6,093,176 | A | 7/2000 | Dennis |
| 6,228,061 | B1 | 5/2001 | Flatland et al. |
| 6,702,787 | B2 | 3/2004 | Racenet et al. |
| 6,942,671 | B1 | 9/2005 | Smith |
| 7,025,747 | B2 | 4/2006 | Smith |
| 7,722,570 | B2 * | 5/2010 | Almond et al. .......... 604/167.06 |
| 2004/0064100 | A1 | 4/2004 | Smith |
| 2005/0010238 | A1 | 1/2005 | Potter et al. |
| 2005/0070851 | A1 | 3/2005 | Thompson et al. |

FOREIGN PATENT DOCUMENTS

| | | |
|---|---|---|
| WO | 02/30305 | 4/2005 |

* cited by examiner

US 8,403,892 B2

CONSTRICTING MECHANISM FOR USE WITH A SURGICAL ACCESS ASSEMBLY

CROSS REFERENCE TO RELATED APPLICATION

This application is a continuation of U.S. application Ser. No. 12/486,164, filed Jun. 17, 2009 now U.S. Pat. No. 7,914,491, which claims the benefit of and priority to U.S. Provisional Application Ser. No. 61/081,483, filed on Jul. 17, 2008, the entire contents of which are incorporated herein by reference.

BACKGROUND

1. Technical Field

The present disclosure relates generally to apparatus and methods for providing percutaneous access to an internal worksite during a surgical procedure. More particularly, the present disclosure relates to a constricting mechanism for use with a surgical access system such, as a trocar or cannula assembly, that is adapted to removably receive a surgical instrument.

2. Background of the Related Art

Minimally invasive surgical procedures are generally performed through small openings in a patient's tissue, as compared to the larger incisions typically required in traditional procedures, in an effort to reduce both patient trauma and recovery time. Access tubes, such as trocars or cannulae, are inserted into the openings in the tissue, and the surgical procedure is carried out by one or more surgical instruments inserted through the lumen which they provide.

In laparoscopic procedures, the patient's abdominal region is typically insufflated, i.e., filled with carbon dioxide, nitrogen gas, or the like, to raise the abdominal wall and provide sufficient working space at the surgical worksite. Accordingly, preventing the escape of the insufflation gases is desirable in order to preserve the insufflated surgical worksite. To this end, surgical access systems generally incorporate a seal adapted to maintain the insufflation pressure.

During the course of a minimally invasive surgical procedure, it is often necessary for a clinician to use different surgical instruments which may vary in size, e.g., diameters. Additionally, a clinician will frequently manipulate the surgical instruments transversely, or side-to-side, in an effort to access different regions of the surgical worksite. This transverse movement may cause the seal to deform, thereby allowing the escape of insufflation gas around the instrument.

While many varieties of seals are known in the art, there exists a continuing need for a mechanism capable of addressing these concerns.

SUMMARY

In one aspect of the present disclosure, a surgical access device is disclosed that is adapted for removable positioning within a percutaneous tissue tract. The surgical access device includes a housing, a constricting mechanism positioned within the housing, and an access sleeve that extends distally from the housing.

The constricting mechanism includes a proximal member in mechanical cooperation with a distal member to permit relative rotation therebetween such that the constricting mechanism is repositionable between a first state and a second state. In the first state, the constricting mechanism is adapted to permit insertion of a surgical instrument, and in the second state, the constricting mechanism is adapted to engage the surgical instrument to limit transverse movement thereof.

The proximal member includes a first plurality of pins extending outwardly therefrom and the distal member includes a second plurality of pins extending outwardly therefrom. Each of the first and second pluralities of pins are configured and dimensioned for engagement with a plurality of rods positioned between the proximal and distal members. The first plurality of pins and the second plurality of pins each correspond in number to the number of rods. Each rod includes a bore formed at a first end and a slot formed at a second end, and each of the first and second pluralities of pins includes a stem portion terminating in a head. The head of each pin defines a transverse dimension that is greater than a transverse dimension defined by the stem portion, and each bore and slot defines a substantially identical transverse dimension that is greater than the transverse dimension defined by the stem portion of each pin, but less than the transverse dimension defined by the head of each pin, such that the pins are securely engagable with the rods.

In one embodiment of the constricting mechanism, the plurality of first pins are positioned within the bores of each of the plurality of rods and the plurality of second pins are positioned within the slots of each the plurality of rods such that relative rotation between the proximal and distal members causes the rods to pivot about the plurality of first pins as the plurality of second pins traverse the slots.

The rods may be arranged in an interlaced configuration to define an opening therebetween that extends through the constricting mechanism. When the constricting mechanism is in the first state, the opening defines a first transverse dimension, and when the constricting mechanism is in the second state, the opening defines a second, smaller transverse dimension.

In another embodiment of the constricting mechanism, at least one of the first and second members includes a tactile member that is configured for manual engagement to facilitate relative rotation between the proximal and distal members.

In yet another embodiment of the constricting mechanism, each rod includes a scalloped portion that is configured and dimensioned to engage an outer surface of the surgical instrument.

In still another embodiment, the constricting mechanism further includes a biasing member that is in mechanical cooperation with at least one of the proximal and distal members to normally bias the constricting mechanism into the second state.

Additionally, or alternatively, the constricting mechanism may include a sleeve connected to the proximal and distal members and defining a passageway therethrough that is configured and dimensioned to receive the surgical instrument. The sleeve is forced into engagement with an outer surface of the surgical instrument as the constricting mechanism is repositioned from the first state into the second state such that a substantially fluid-tight seal is formed between the constricting mechanism and the surgical instrument. The sleeve may be formed of a resilient material such that the passageway enlarges as the constricting mechanism is repositioned from the second state into the first state to facilitate removal of the surgical instrument.

In another embodiment, the constricting mechanism may further include at least one seal member associated with at least one of the proximal and distal members and adapted to form a substantially fluid tight seal with the surgical instrument upon insertion.

In an alternate aspect of the present disclosure, a method of establishing percutaneous access to a surgical worksite is disclosed. The method includes the provision of a surgical access assembly having a housing, a constricting mechanism positioned within the housing and including a proximal member in mechanical cooperation with a distal member to permit relative rotation therebetween, and an access sleeve extending distally from the housing. The method further includes the steps of positioning the surgical access device within tissue, inserting the surgical instrument into the surgical access device, and effectuating relative rotation between the proximal and distal members of the constricting mechanism such that the constricting mechanism engages the surgical instrument to limit transverse movement thereof.

In another aspect of the present disclosure, a method of manufacturing a constricting mechanism for use with a surgical access device to limit transverse movement of a surgical instrument inserted therethrough. The method includes the steps of providing a proximal member including a first plurality of pins extending outwardly therefrom, providing a distal member including a second plurality of pins extending outwardly therefrom, providing a plurality of rods including structure adapted to receive one of the first plurality of pins and one of the second plurality of pins, and positioning the rods between the proximal and distal members such that the rods receive one of the first plurality of pins and one of the second plurality of pins to permit relative rotation between the proximal and distal members. Relative rotation between the proximal and distal members repositions the constricting mechanism between a first state, in which the constricting mechanism is adapted to permit insertion of the surgical instrument, and a second state, in which the constricting mechanism is adapted to engage the surgical instrument to limit transverse movement thereof.

BRIEF DESCRIPTION OF THE DRAWINGS

Various embodiments of the present disclosure are described herein below with references to the drawings, wherein.

DETAILED DESCRIPTION

Figure 1:
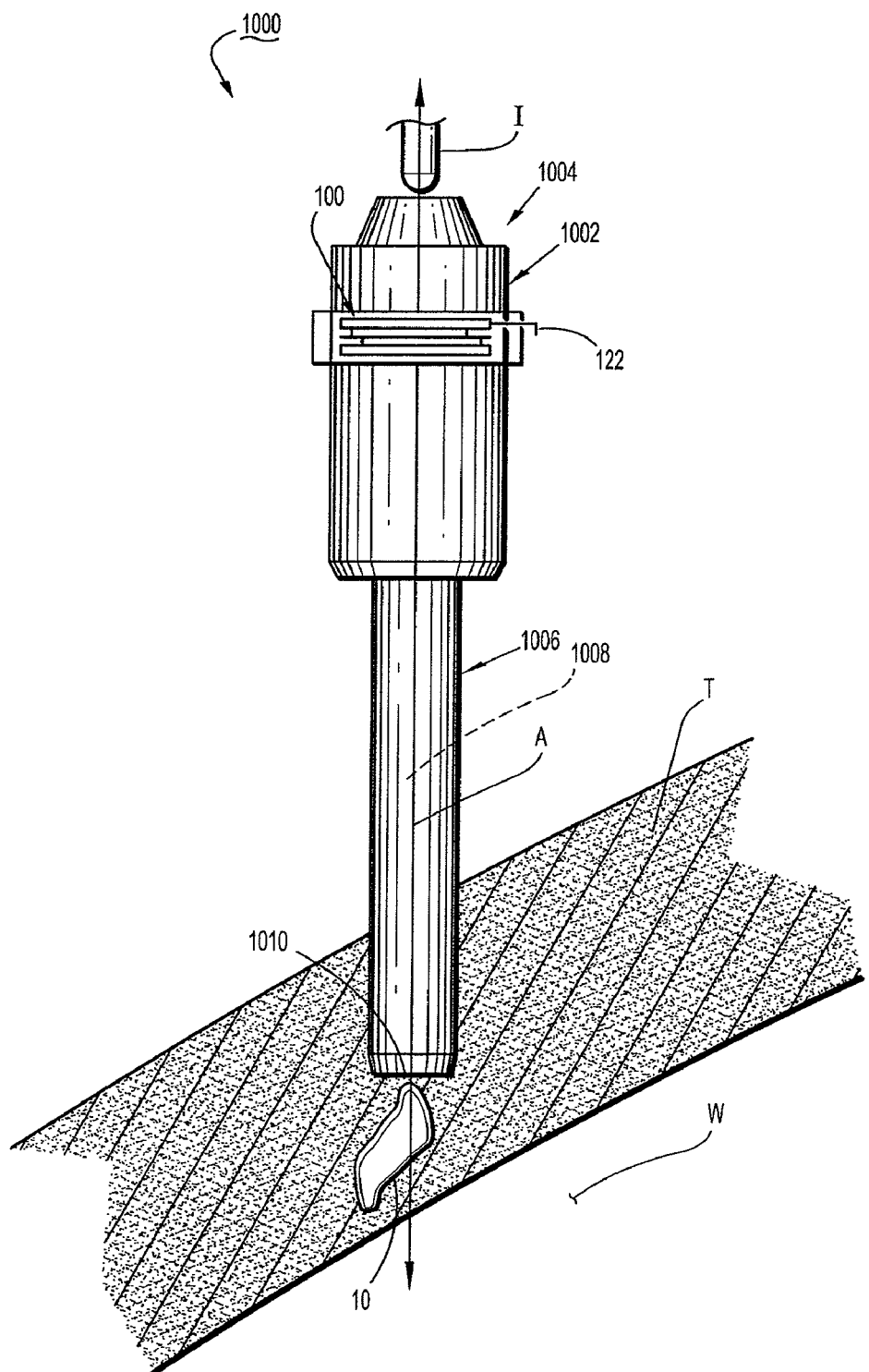
FIG. 1 is a side, schematic view of a surgical access assembly including one embodiment of a constricting mechanism in accordance with the principles of the present disclosure.
Figure 2:
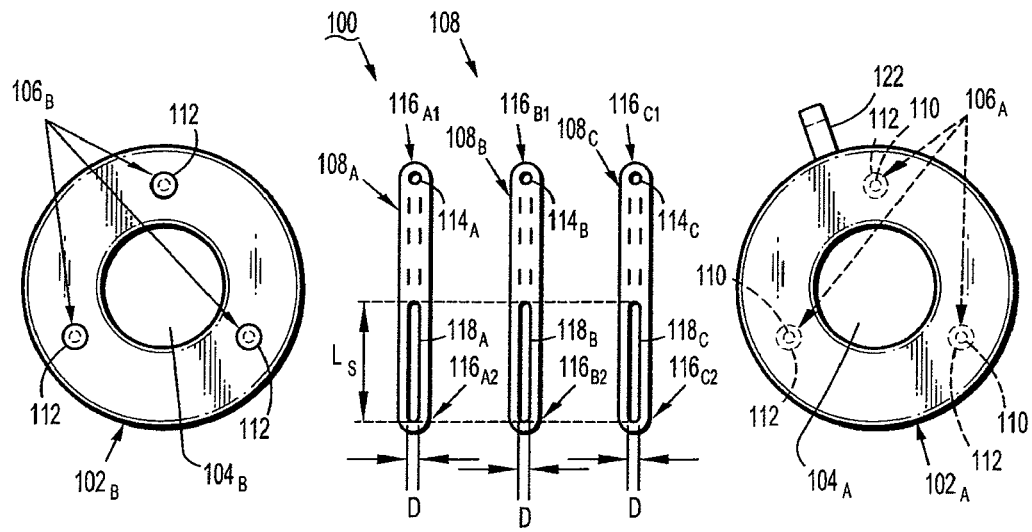
FIG. 2 is a top, plan view of the constricting mechanism seen in FIG. 1 with parts separated.
Figure 3:
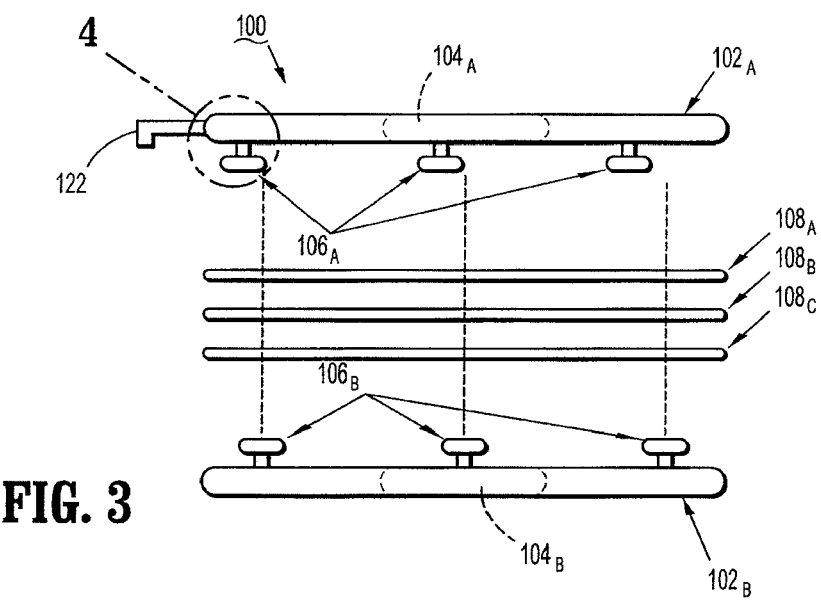
FIG. 3 is a side, plan view of the constricting mechanism seen in FIG. 1 with parts separated.

In the drawings and in the description which follows, in which like references numbers identify similar or identical elements, the term "proximal" will refer to the end of an instrument or component that is closest to the clinician during use, while the term "distal" will refer to the end that is furthest from the clinician. Additionally, use of the term "surgical instrument" throughout the present disclosure should be understood to include any surgical instrument that may be employed during the course of a minimally invasive surgical procedure, including but not limited to an obturator, a surgical fastening apparatus, a viewing scope, or the like. Finally, the term "transverse" should be understood as referring to any axis, or movement along any axis, that intersects the longitudinal axis of an instrument or component.

FIG. 1 illustrates a surgical access assembly 1000 having a housing 1002 at a proximal end 1004 thereof and an access sleeve 1006 which extends distally therefrom along a longitudinal axis "A". The housing 1002 is configured and dimensioned to accommodate a constricting mechanism 100, which will be described in detail below, and may be any structure suitable for this intended purpose. Further information regarding the housing 1002 may be obtained through reference to commonly owned U.S. Pat. No. 7,169,130 to Exline et al., the entire contents of which are incorporated by reference.

The access sleeve 1006 is configured and dimensioned for positioning with a tissue tract 10 formed in a patient's tissue "T", which can be either pre-existing or created by the clinician through the use of a scalpel, for example. The access sleeve 1006 defines a lumen 1008 and an open distal end 1010 to permit the passage of one or more surgical instruments "I" therethrough to facilitate percutaneous access to a surgical worksite "W" removed from the patient's tissue "T" with the surgical instrument "I".

Referring now to FIGS. 2-6 as well, one embodiment of the constricting mechanism 100 will be discussed. The constricting mechanism 100 includes a proximal member $102_A$ and a distal member $102_B$ in mechanical cooperation such that the respective proximal and distal members $102_A$, $102_B$ are adapted for relative rotation. The proximal and distal members $102_A$, $102_B$ define respective apertures $104_A$, $104_B$ that are configured and dimensioned to accommodate passage of the surgical instrument "I" therethrough. While the respective proximal and distal members $102_A$, $102_B$ are illustrated as substantially annular structures, any suitable configuration may be employed, including polygonal configurations such as triangular, square, or hexagonal. The respective proximal and distal members $102_A$, $102_B$ may be formed of any suitable biocompatible material, including but not being limited to polymeric materials.

To facilitate relative rotation between the proximal and distal members $102_A$, $102_B$, the proximal and distal members $102_A$, $102_B$ include a plurality of pins $106_A$, $106_B$, respectively, that are engagable with a plurality of rods 108. The plurality of pins $106_A$, $106_B$ correspond in number to the number of rods 104, and accordingly, in the embodiment seen in FIGS. 1-6, the proximal member $102_A$ includes three pins $106_A$ and the distal member $102_B$ includes three pins $106_B$ corresponding to a first rod $104_A$, a second rod $104_B$, and a third rod $104_C$. In alternate embodiments, however, the constricting mechanism 100 may include fewer or greater numbers of pins $106_A$, $106_B$ and rods 108.

Figure 4:
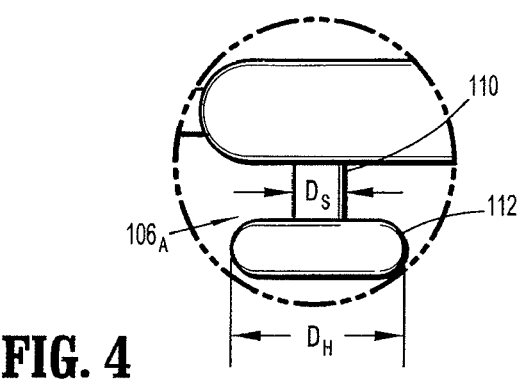
FIG. 4 is an enlarged view of the section indicated in FIG. 3.

The pins $106_A$ depend downwardly from the proximal member $102_A$, i.e., towards the distal member $102_B$, whereas the pins $106_B$ depend upwardly from the distal member $102_B$, i.e., towards the proximal member $102_A$. Each of the pins $106_A$, $106_B$ includes a stem portion 110 that terminates in a head 112. The stem portion 110 defines a transverse dimension "$D_S$" and the head 112 defines a transverse dimension "$D_H$". As best seen in FIG. 4, the transverse dimension "$D_H$" defined by the head 112 is greater than the transverse "$D_S$" defined by the stem portion 110.

Each of the plurality of rods $108_A$, $108_B$, $108_C$ includes a bore and a slot formed at opposite ends thereof that are configured and dimensioned to receive the pins $106_A$, $106_B$ included on the proximal and distal members $102_A$, $102_B$, respectively. Specifically, the first rod $108_A$ includes a bore $114_A$ at a first end $116_{A1}$ and a slot $118_A$ at a second end $116_{A2}$, the second rod $108_B$ includes a bore $114_B$ at a first end $116_{B1}$ and a slot $118_B$ at a second end $116_{B2}$, and the third rod $108_C$ includes a bore $114_C$ at a first end $116_{C1}$ and a slot $118_C$ at a second end $116_{C2}$. The bores $114_A$, $114_B$, $114_C$ and the slots $118_A$, $118_B$, $118_C$ each define a transverse dimension "D" that is greater than the transverse dimension "$D_S$" defined by the stem portion 110 of the pins $106_A$, $106_B$, but less than the transverse dimension "$D_H$" defined by the head 112, such that the pins $106_A$, $106_B$ can be inserted through the bores $114_A$, $114_B$, $114_C$ and the slots $118_A$, $118_B$, $118_C$, respectively, and thereby securely engage the rods $108_A$, $108_B$, $108_C$. In the particular embodiment of the constricting mechanism 100 seen in FIGS. 1-6, the bores $114_A$, $114_B$, $114_C$ receive the pins $106_A$ included on the proximal member $102_A$ while the slots $118_A$, $118_B$, $118_C$ receive the pins $106_B$ included on the distal member $102_B$. In an alternate embodiment, however, the bores $114_A$, $114_B$, $114_C$ may receive the pins $106_B$ included on the distal member $102_B$ while the slots $118_A$, $118_B$, $118_C$ receive the pins $106_A$ included on the proximal member $102_A$.

Figure 5:
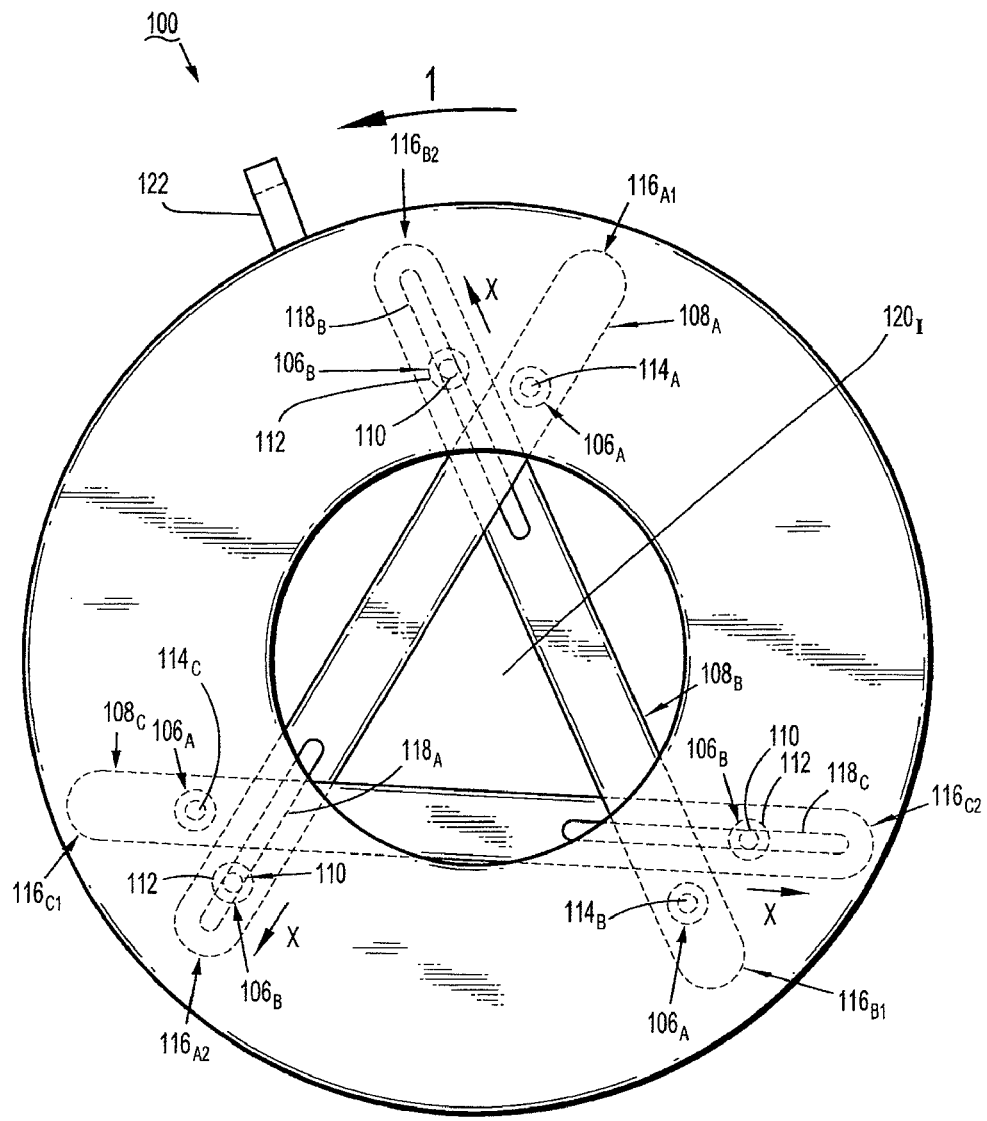
FIG. 5 is a top, schematic view of the constricting mechanism seen in FIG. 1 shown in an open state prior to the insertion of a surgical instrument.
Figure 6:
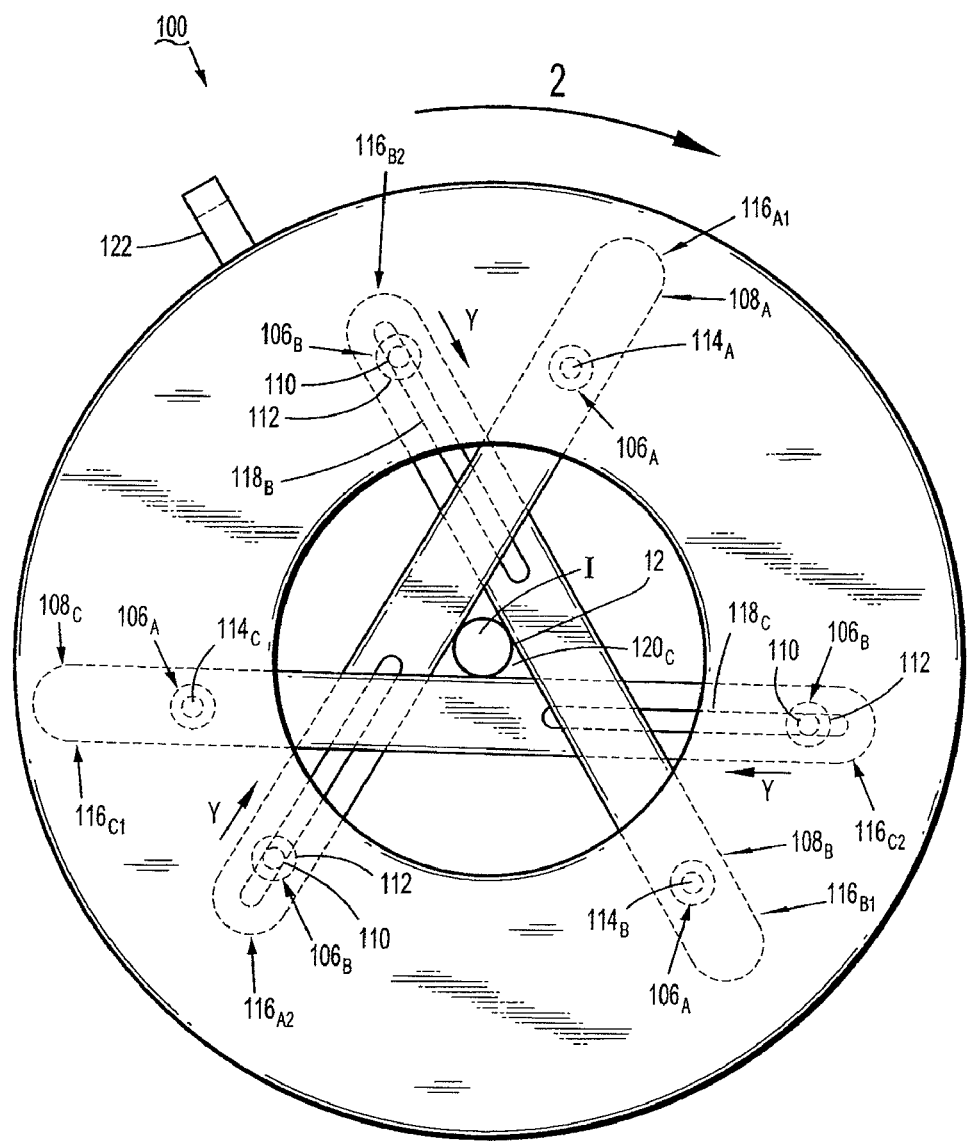
FIG. 6 is a top, schematic view of the constricting mechanism seen in FIG. 1 shown in a constricted state with a surgical instrument inserted therethrough.

The slots $118_A$, $118_B$, $118_C$ extend along the rods $108_A$, $108_B$, $108_C$ to define a length "$L_S$" that is dimensioned to accommodate relative movement between the rods $108_A$, $108_B$, $108_C$ and the pins $106_A$, $106_B$ which they receive during manipulation of the constricting mechanism 100, as described in further detail below. Upon assembly of the constricting mechanism 100, the rods $108_A$, $108_B$, $108_C$ are interlaced such that an opening $120_I$ is defined therebetween. As seen in FIGS. 5-6, the rods $108_A$, $108_B$, $108_C$ are arranged such that the first end $116_{A1}$ of the rod $108_A$ is positioned on top of the second end $116_{B2}$ of the of the rod $108_B$, the second end $116_{A2}$ of the rod $108_A$ is positioned beneath the first end $116_{C1}$ of the rod $108_C$, and the first end $116_{B1}$ of the rod $108_B$ is positioned on top of the second end $116_{C2}$ of the rod $108_C$. However, other arrangements of the rods $108_A$, $108_B$, $108_C$ in alternate embodiments of the constricting mechanism 100 are also within the scope of the present disclosure.

Referring still to FIGS. 1-6, operation of the constricting mechanism 100 will be described in conjunction with the surgical access system 1000. Initially, i.e., prior to insertion of the surgical instrument "I", the constricting mechanism 100 is in an open state (FIG. 5) in which the opening $120_I$ defined between the rods $108_A$, $108_B$, $108_C$ is dimensioned to allow the surgical instrument "I" to pass therethrough substantially uninhibited. After insertion of the surgical instrument "I", the clinician effectuates relative rotation between the proximal and distal members $102_A$, $102_B$, for example, by rotating the proximal member $102_A$ relative to the distal member $102_B$ in the direction of arrow 1. To facilitate rotation of the proximal member $102_A$, in one embodiment, the proximal member $102_A$ includes a tactile member 122 that extends through the housing 1002 of the surgical access system 1000 (FIG. 1) for manual engagement by the clinician.

Relative rotation between the respective proximal and distal members $102_A$, $102_B$ causes the rods $108_A$, $108_B$, $108_C$ to pivot about the pins $106_A$ extending through their respective bores $114_A$, $114_B$, $114_C$. As the rods $108_A$, $108_B$, $108_C$ pivot, the pins $106_B$ outwardly traverse the slots $118_A$, $118_B$, $118_C$ through which they extend in the direction indicated by arrow "X". The clinician continues to rotate the proximal member $102_A$ until the constricting mechanism is transitioned into a constricted state (FIG. 6) in which the rods $108_A$, $108_B$, $108_C$ define a narrowed opening $120_C$ and engage an outer surface 12 of the surgical instrument "I". The engagement of the rods $108_A$, $108_B$, $108_C$ with the surgical instrument "I" substantially limits any transverse movement of the surgical instrument "I" within the constricting mechanism 100, and thus, within the surgical access system 1000 (FIG. 1).

Figure 7:
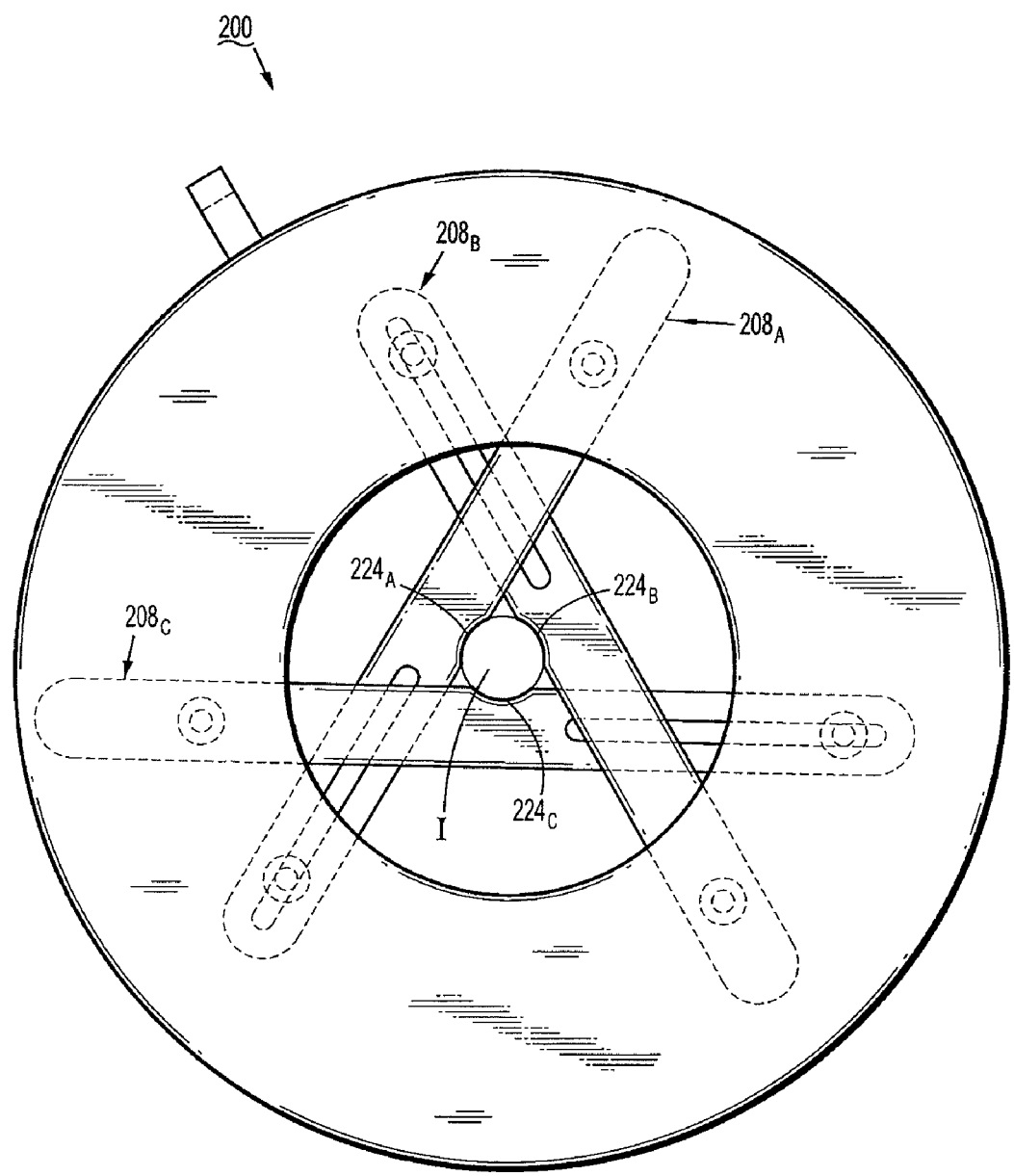
FIG. 7 is a top, schematic view of another embodiment of the constricting mechanism seen in FIG. 1.

As seen in FIG. 7, in one embodiment, the constricting mechanism 200 may include rods $208_A$, $208_B$, $208_C$ having scalloped portions $224_A$, $224_B$, $224_C$, respectively, to increase the surface area of each rod $208_A$, $208_B$, $208_C$ that is in contact with the surgical instrument "I" in the constricted state.

Referring again to FIGS. 1-6, to remove the surgical instrument "I" from the constricting mechanism 100, the clinician returns the constricting mechanism 100 to the open state (FIG. 5) by rotating the proximal member $102_A$ in the direction of arrow 2. As the constricting mechanism 100 transitions from the constricted state to the open state, the rods $108_A$, $108_B$, $108_C$ again pivot about the pins $106_A$, and the pins $106_B$ inwardly traverse the slots $118_A$, $118_B$, $118_C$ in the direction indicated by arrow "Y". The clinician continues to rotate the proximal member $102_A$ until the surgical instrument "I" can be withdrawn from the constricting mechanism 100. Alternatively, however, if the configuration and dimensions of the surgical instrument "I" allow, the clinician can simply withdraw the surgical instrument "I" in the proximal direction while the constricting mechanism 100 is in the constricted state.

Figure 8:
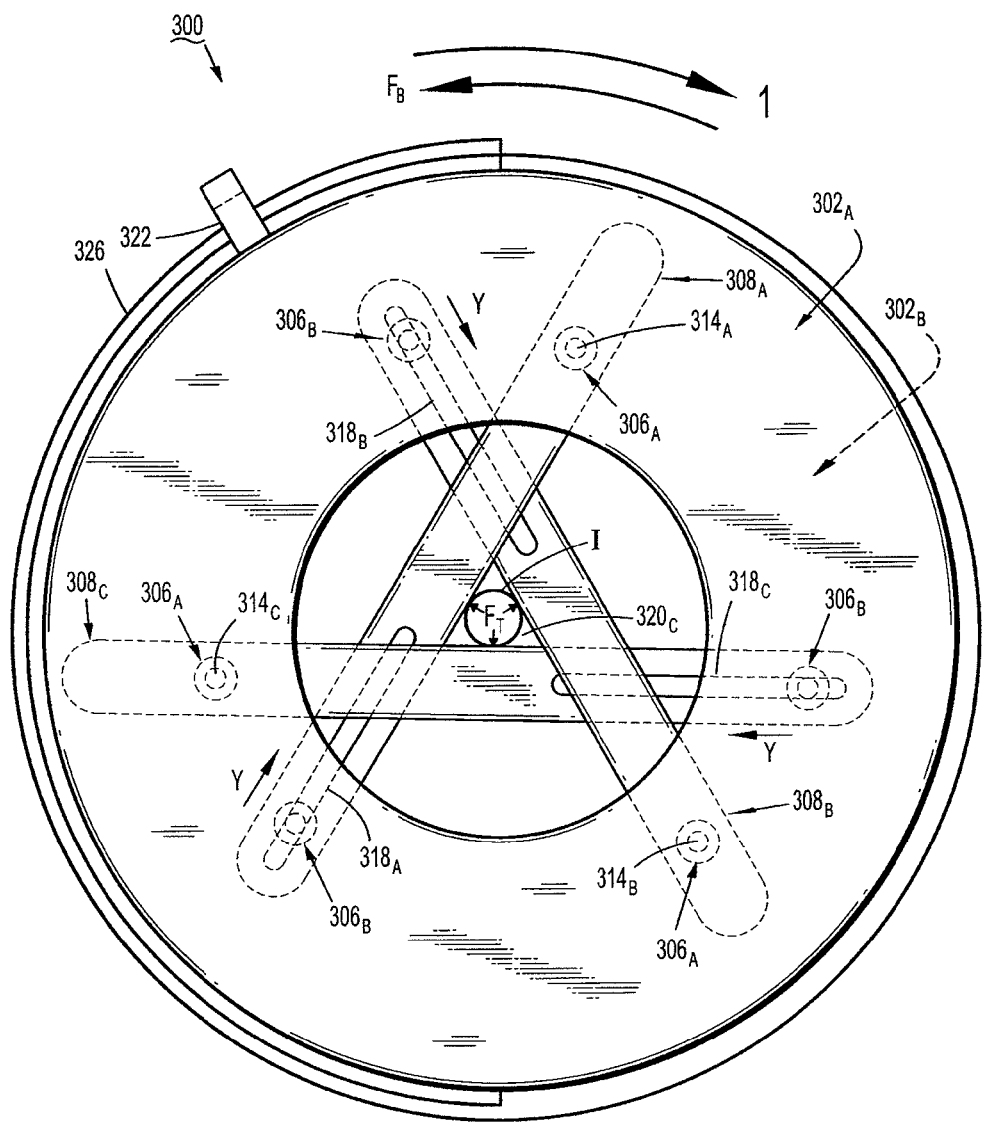
FIG. 8 is a top, schematic view of yet another embodiment of the constricting mechanism seen in FIG. 1 including a biasing member and shown in a constricted state.
Figure 9:
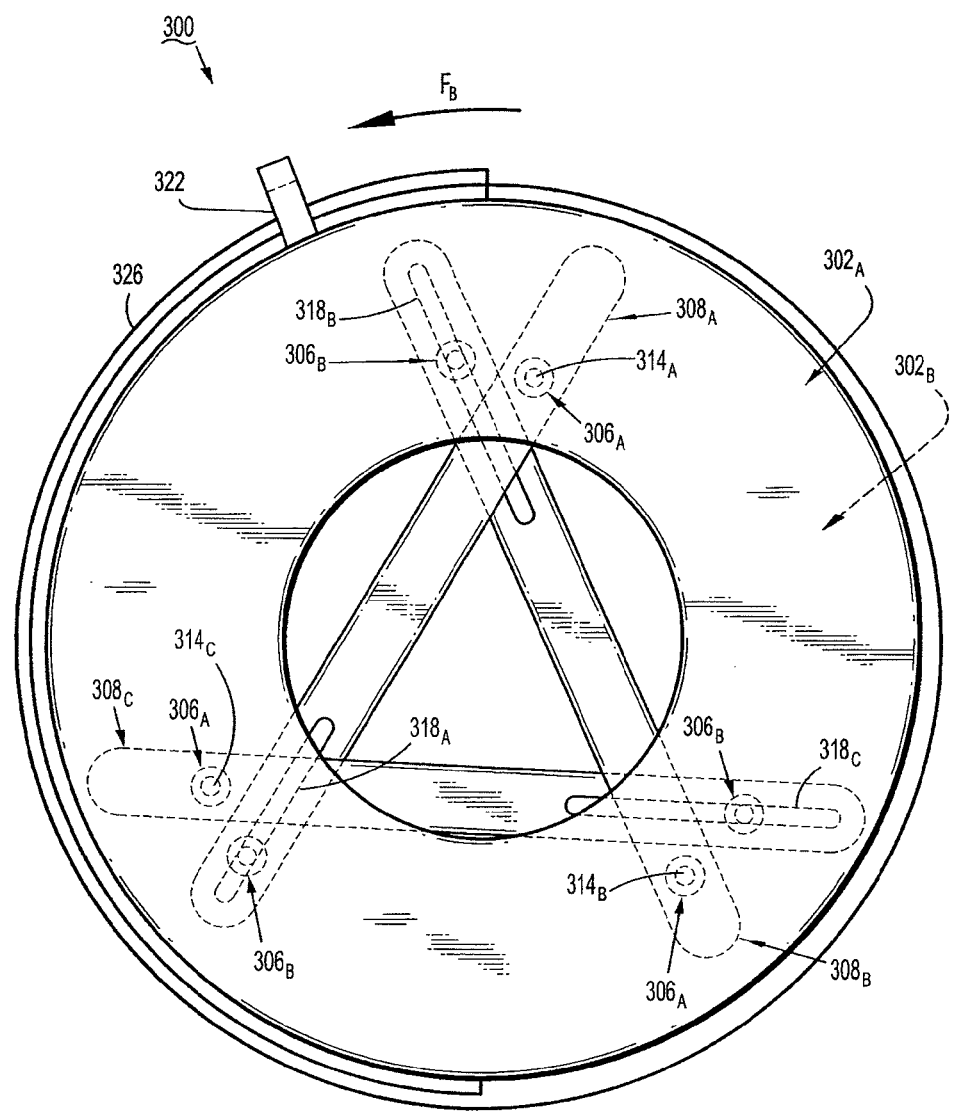
FIG. 9 is a top, schematic view of the constricting mechanism seen in FIG. 8 shown in an open state.

Referring now to FIGS. 8-9, in an alternate embodiment, the constricting mechanism 300 may include a biasing member 326, such as a torsion spring or the like, in mechanical cooperation with the respective proximal and distal members $302_A$, $302_B$. The biasing member 326 applies a biasing force "$F_B$" to the respective proximal and distal members $302_A$, $302_B$ which acts to normally bias the constricting mechanism 300 towards the constricted state (FIG. 8). In this embodiment, as the clinician rotates the proximal member $302_A$ in the direction of arrow 1, the biasing force "$F_B$" is overcome, and the constricting mechanism 300 transitions from the constricted state to the open state (FIG. 9).

To effectuate such rotation, the clinician can either manually displace the tactile member 322 in the direction of arrow 1, as discussed above with respect to the embodiment seen in FIGS. 1-6, or alternatively, if the configuration and dimensions of the surgical instrument "I" allow, the clinician can simply force the surgical instrument "I" through the opening $320_C$ defined by the constricting mechanism 300 in the constricted state. As the surgical instrument "I" is forced distally through the opening $320_C$, the surgical instrument "I" applies a transverse force "$F_T$" to the rods $308_A$, $308_B$, $308_C$ that is directed radially outward. The transverse force "$F_T$" causes the rods $308_A$, $308_B$, $308_C$ to pivot about the pins $306_A$ extending through their respective bores $314_A$, $314_B$, $314_C$. As the rods $308_A$, $308_B$, $308_C$ pivot, the pins $306_B$ inwardly traverse the slots $318_A$, $318_B$, $318_C$ in the direction of arrows "Y", thereby effectuating relative rotation between the respective proximal and distal members $302_A$, $302_B$ and enlarging the opening $320_C$.

When the clinician seeks to remove the surgical instrument "I", the clinician can either return the constricting mechanism 300 to the open state (FIG. 9) by displacing the tactile member 322 in the direction of arrow 1 and effectuating relative rotation between the respective proximal and distal members $302_A$, $302_B$, or alternatively, the clinician can simply withdraw the surgical instrument "I" from the constricting mechanism 300 in the proximal direction, if the configuration and dimensions of the surgical instrument "I" allow.

In an alternate embodiment, the constricting mechanism may further include a motor and worm gear assembly in mechanical cooperation with the constricting mechanism to regulate the reciprocal transitioning between the open and constricted states thereof. Employing a motor and worm gear assembly may allow the constricting mechanism to check the transverse force applied to the rods by the surgical instrument upon insertion such that the rods will not be spread apart.

Figure 10:
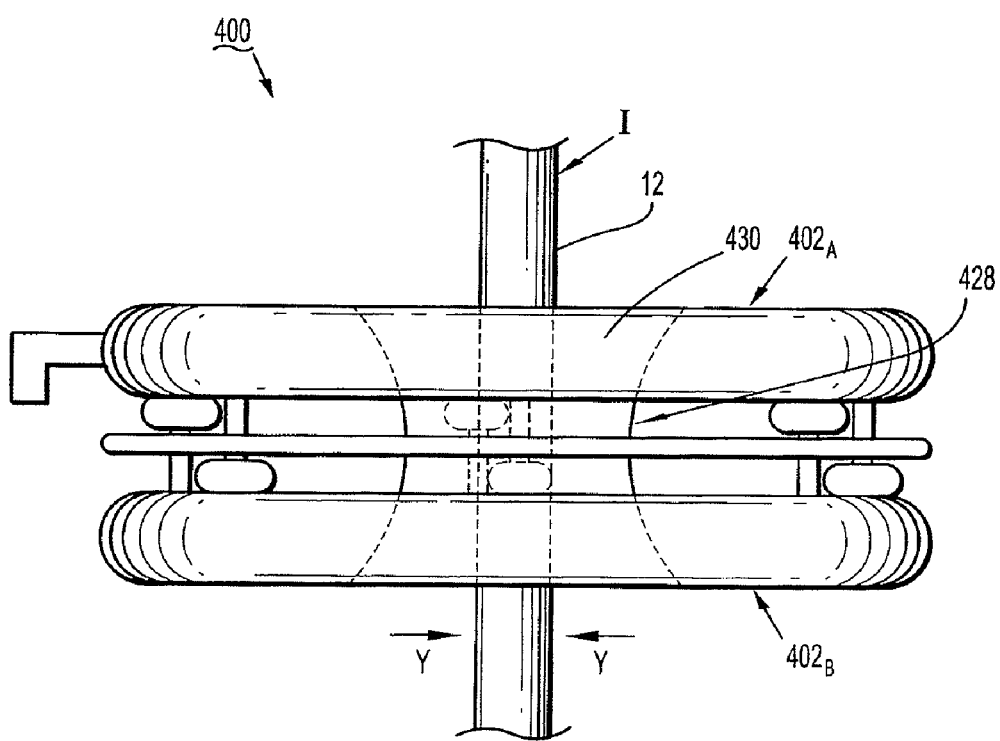
FIG. 10 is a side, schematic view of still another embodiment of the constricting mechanism seen in FIG. 1 including a tubular sleeve and shown in an open state with a surgical instrument inserted therethrough.
Figure 11:
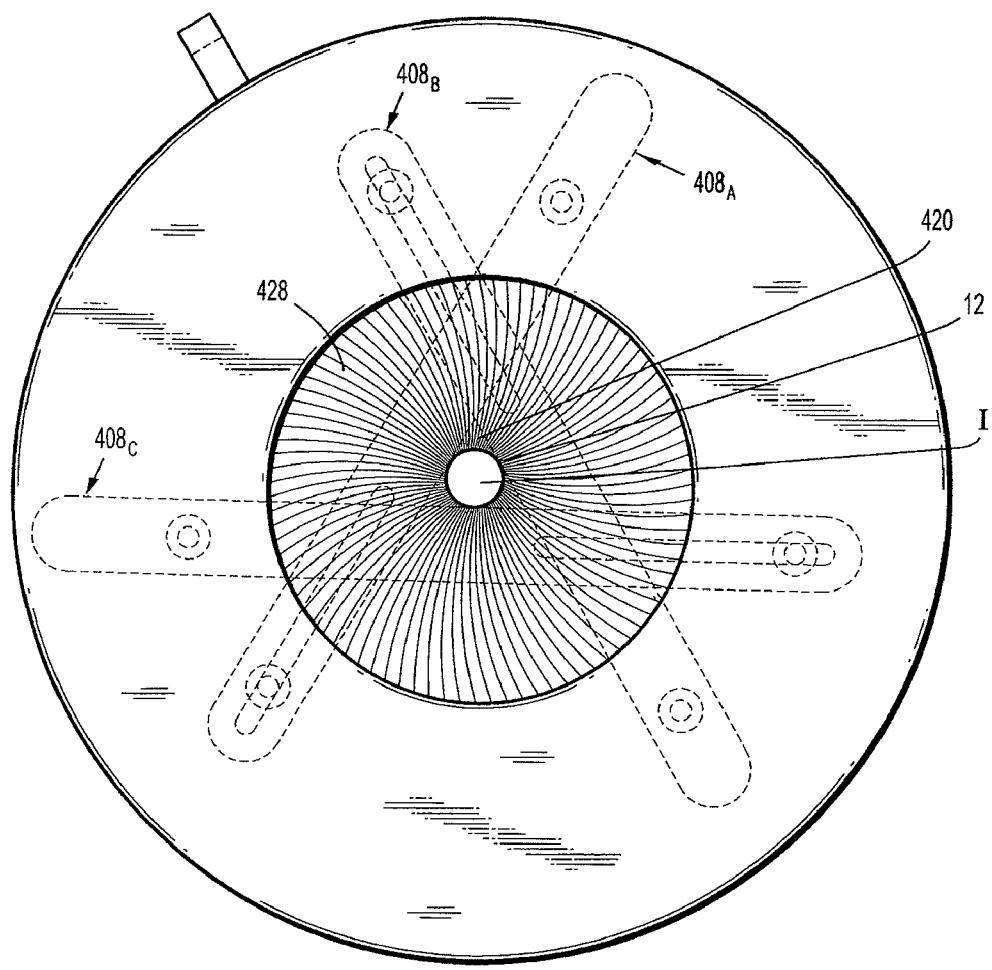
FIG. 11 is a top, schematic view of the constricting mechanism seen in FIG. 10 shown a constricted state.

Referring now to FIGS. 10-11, an alternate embodiment of the constricting mechanism, referred to generally by reference number 400, will be discussed. The constricting mechanism 400 is substantially similar to the constricting mechanism 100 that was discussed above with respect to FIGS. 1-6, and accordingly, will only be discussed with respect to its differences therefrom.

The constricting mechanism 400 includes a tubular sleeve 428 positioned within the opening 420 defined between the rods $408_A$, $408_B$, $408_C$. The tubular sleeve 428 is connected to the respective proximal and distal members $402_A$, $402_B$ in any suitable manner, including but not limited to integral formation therewith or the use of an adhesive. The tubular sleeve 428 defines a passageway 430 therethrough that is configured and dimensioned to receive the surgical instrument "I". In the embodiment seen in FIGS. 10-11, the tubular sleeve 428 defines an inwardly tapered configuration to facilitate insertion of the surgical instrument "I" through the passageway 430. The tubular sleeve 428 may be formed of any biocompatible material that is at least semi-resilient in nature, and in one embodiment, may be adapted to close the passageway 430 in the absence of the surgical instrument "I".

Following insertion of the surgical instrument "I", the constricting mechanism 400 is transitioned from the open state seen in FIG. 10 to the constricted state seen in FIG. 11. During this transition, the rods $408_A$, $408_B$, $408_C$ deform the tubular sleeve 428 inwardly in the direction of arrows "Y". As the tubular sleeve 428 deforms, the tubular sleeve 428 engages the outer surface 12 of the surgical instrument "I" to form a substantially fluid-tight seal therewith. Accordingly, when in the constricted state, the constricting member 400 serves not only to restrict transverse movement of the surgical instrument "I" inserted therethrough, as described above with respect to the embodiment of FIGS. 1-6, but also to substantially prevent the escape of insufflation gas.

As the constricting mechanism 400 is returned to the open state, the resilient nature of the material comprising the tubular sleeve 428 allows the passageway 430 to re-open, thereby facilitating the removal of the surgical instrument "I" and the insertion of a subsequent instrument, if necessary.

Figure 12:
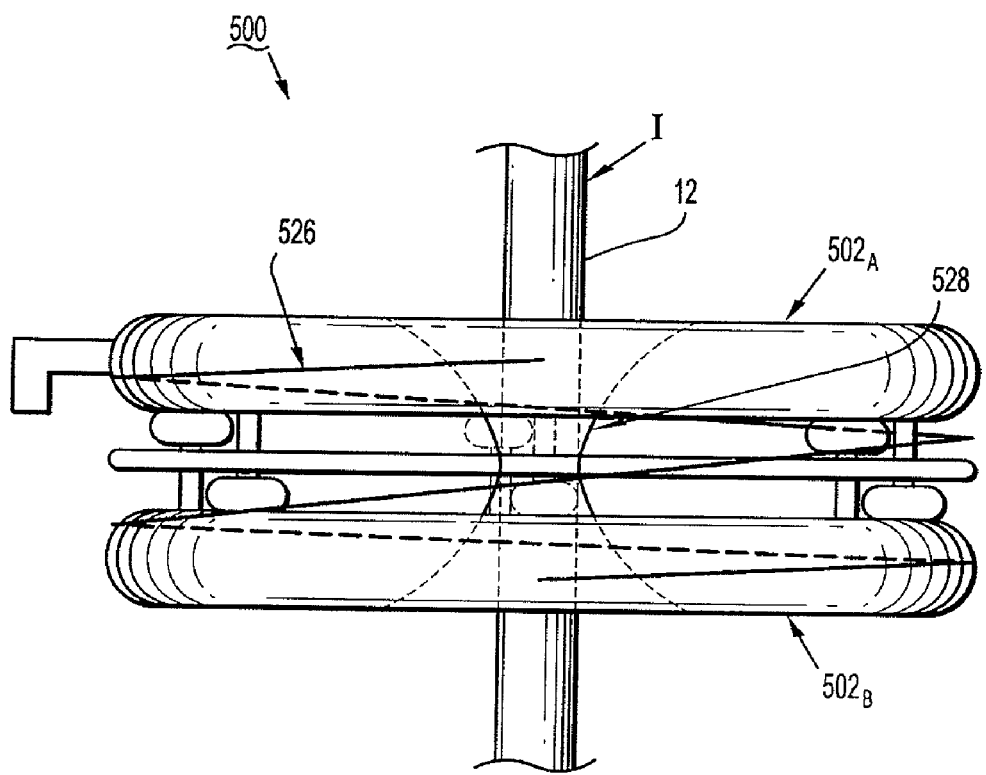
FIG. 12 is a side, schematic view of one embodiment of the constricting mechanism seen in FIG. 10 including a biasing member and shown a constricted state subsequent to the insertion of a surgical instrument through the tubular sleeve.

FIG. 12 illustrates an alternate embodiment of the constricting mechanism, referred to generally by the reference umber 500. The constricting mechanism 500 is substantially similar to the constricting mechanism 400 discussed with respect to FIGS. 10-11, but for the incorporation of a biasing member 526, such as a torsion spring or the like. The biasing member 526 is in mechanical cooperation with the respective proximal and distal members $502_A$, $502_B$. As discussed above with respect to the embodiment of the constricting mechanism 300 seen in FIGS. 8-9, the biasing member 526 acts to normally bias the constricting mechanism 500 towards the constricted state thereof in which the tubular sleeve 528 engages the outer surface 12 of the surgical instrument "I" to form a substantially fluid-tight seal therewith.

Figure 13:
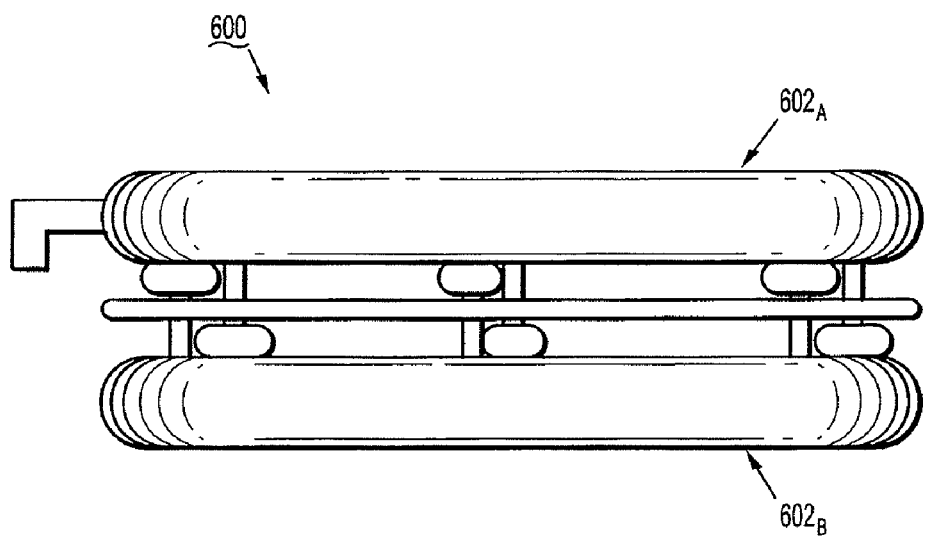
FIG. 13 is a side, schematic view of another embodiment of the constricting mechanism seen in FIG. 1 including a seal member.
Figure 14:
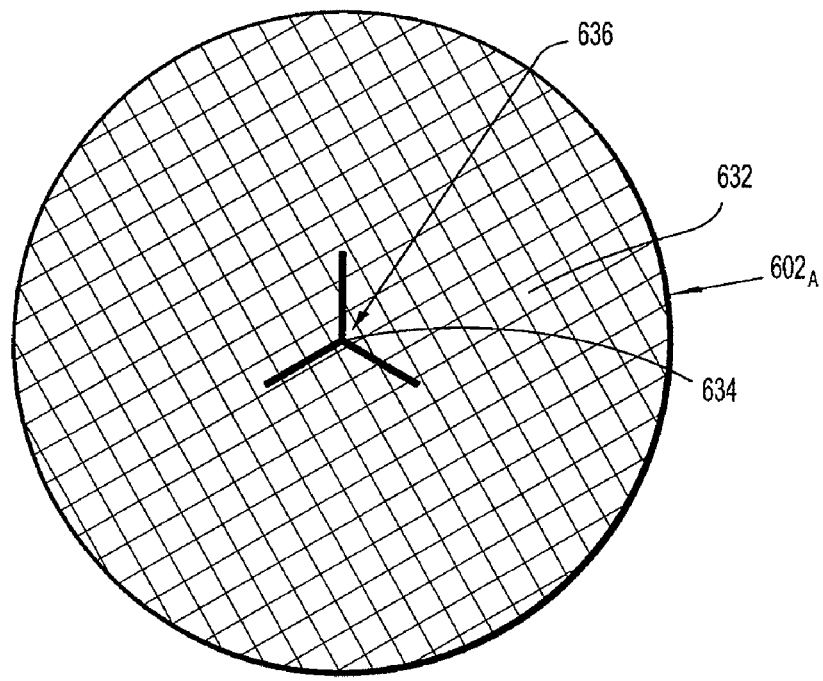
FIG. 14 is a top view of the constricting mechanism seen in FIG. 13 illustrating the seal member prior to the insertion of a surgical instrument.
Figure 15:
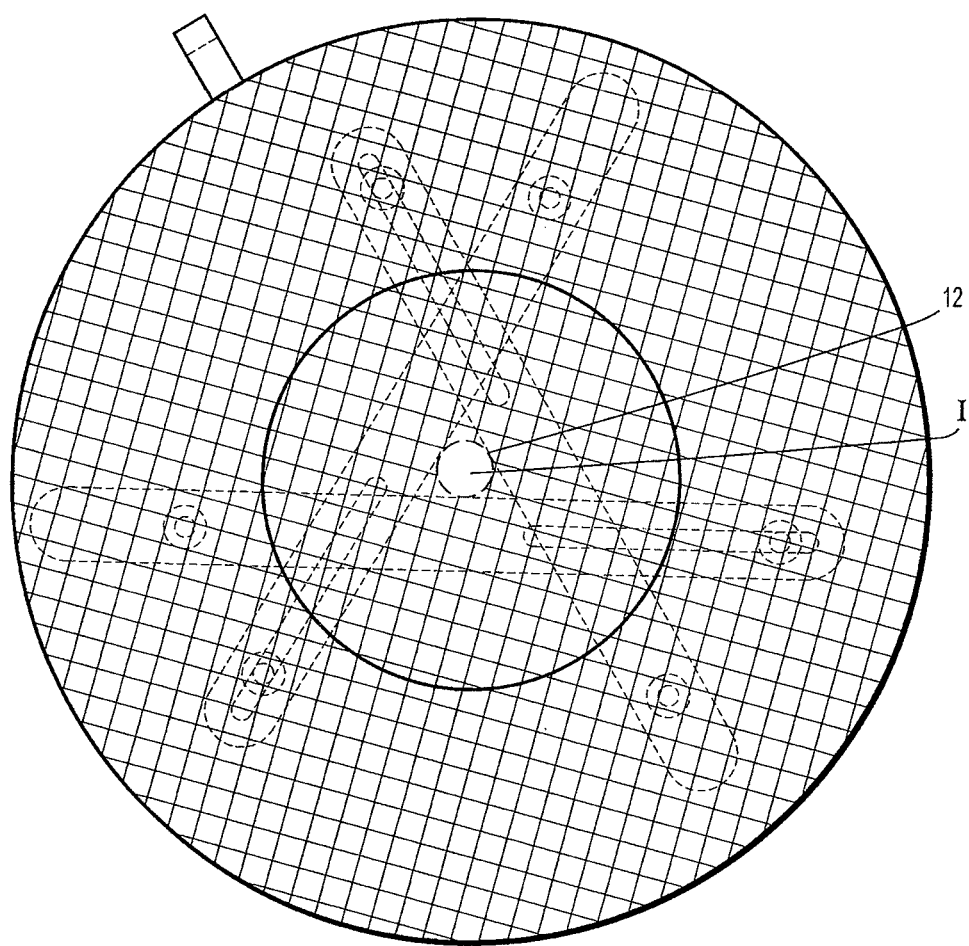
FIG. 15 is a top, schematic view of the constricting mechanism seen in FIG. 14 shown in a constricted state and illustrating the seal member with a surgical instrument inserted therethrough.

With reference now to FIGS. 13-15, another embodiment of the constricting mechanism, referred to generally by reference number 600, will be discussed. The constricting mechanism 600 is substantially similar to the constricting mechanism 100 discussed above with respect to FIGS. 1-6, and accordingly, will only be discussed with respect to its differences therefrom.

The constricting mechanisms 600 includes a seal member 632 defining an aperture 634 therethrough that is adapted to close in the absence of a surgical instrument "I" to substantially prevent the escaped of insufflation gas through the constricting mechanism 600. The seal member 632 may include any structure suitable for this intended purpose, including but not limited to a tricuspid valve 636, as best seen in FIG. 14, or a slit-valve. In the embodiment seen in FIGS. 13-15, the constricting mechanism 600 includes a single seal member 632 that is associated with the proximal member $602_A$. However, the seal member 632 may alternatively be associated with the distal member $602_B$. Additionally, the present disclosure contemplates an embodiment of the constricting mechanism 600 which includes multiple seal members 632 i.e., first and second seal members, that are respectively associated with the proximal and distal members $602_A$, $602_B$.

Upon insertion of the surgical instrument "I" into the constricting mechanism 600, the aperture 634 defined by the seal member 632 is enlarged and substantially conforms to the outer surface 12 of the surgical instrument "I" such that a substantially fluid-tight seal is formed therewith. Accordingly, the constricting member 600 seen in FIGS. 13-15 may be employed to not only restrict transverse movement of the surgical instrument "I" upon insertion, as described above with respect to the embodiment seen in FIGS. 1-6, but also to substantially prevent the escape of insufflation gas.

Figure 16:
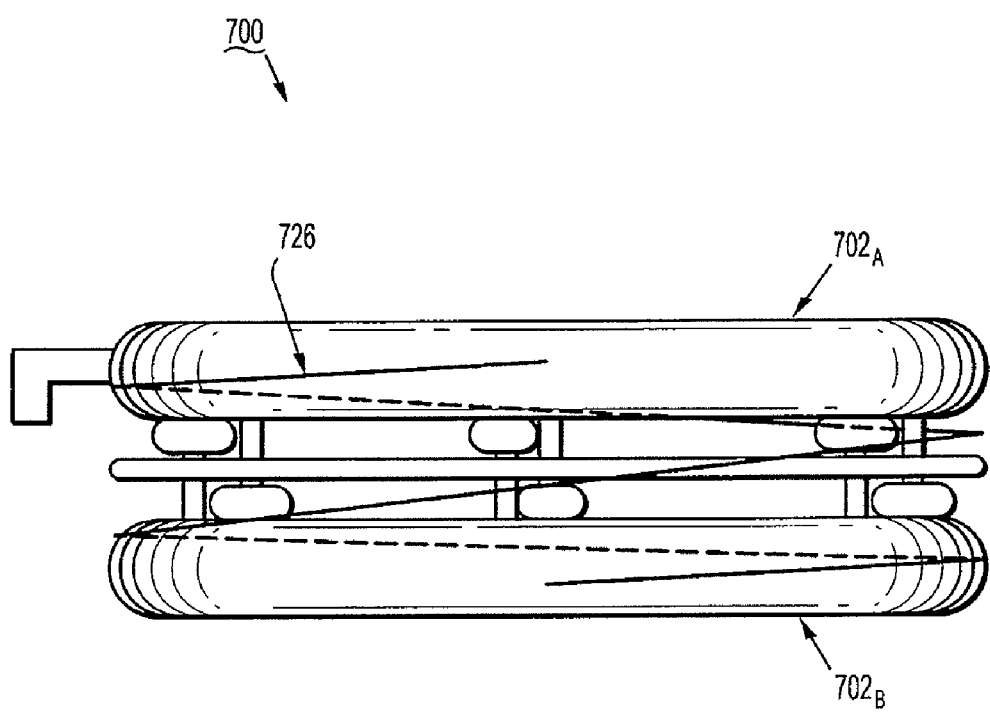
FIG. 16 is a side, schematic view of one embodiment of the constricting mechanism seen in FIG. 13 including a biasing member.

FIG. 16 illustrates an alternate embodiment of the constricting mechanism, referred to generally by reference number 700. The constricting mechanism 700 is substantially similar to the constricting mechanism 600 discussed with respect to FIGS. 13-15, but for the incorporation of a biasing member 726, such as a torsion spring or the like. The biasing member 726 is in mechanical cooperation with the respective proximal and distal members $702_A$, $702_B$. As discussed above with respect to the embodiment seen in FIGS. 8-9, the biasing member 726 acts to normally bias the constricting mechanism 700 towards the constricted state thereof to facilitate the secure engagement of a surgical instrument (not shown) to substantially limit transverse movement thereof.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described above. For example, each embodiment of the constricting mechanism discussed herein above has been described as including a proximal member that is rotated relative to a distal member to transition the constricting mechanism between open and constricted states. It should be appreciated, however, that the constricting mechanism may alternatively be caused to transition between the open and constricted states by rotating the distal member relative to the proximal member. Various other changes and modifications may also be implemented by one skilled in the art without departing from the scope or spirit of the present disclosure

What is claimed:

1. A method of manufacturing a constricting mechanism for use with a surgical access device to limit transverse movement of a surgical instrument inserted therethrough, comprising the steps of:
    providing a proximal member including a first plurality of pins extending outwardly therefrom;
    providing a distal member including a second plurality of pins extending outwardly therefrom;
    providing a plurality of rods including structure adapted to receive one of the first plurality of pins and one of the second plurality of pins; and
    positioning the plurality of rods between the proximal and distal members such that the plurality of rods each receive one of the first plurality of pins and one of the second plurality of pins to permit relative rotation between the proximal and distal members such that the constricting mechanism is repositionable between a first state, in which the constricting mechanism is adapted to permit insertion of the surgical instrument, and a second state, in which the constricting mechanism is adapted to engage the surgical instrument to limit transverse movement thereof.

2. The method of claim 1, wherein the step of providing the plurality of rods includes providing the plurality of rods as substantially linear rods.

3. The method of claim 1, wherein the steps of providing the proximal and distal members include providing the proximal and distal members such that the first plurality of pins and the second plurality of pins each correspond in number to the number of rods.

4. The method of claim 1, wherein the steps of providing the proximal and distal members include providing at least one of the proximal and distal members with a tactile member configured for manual engagement to facilitate relative rotation between the proximal and distal members.

5. The method of claim 1, wherein the step of providing the plurality of rods includes providing each rod with a scalloped portion configured and dimensioned to engage an outer surface of the surgical instrument.

6. The method of claim 1 further comprising mechanically connecting a biasing member to at least one of the proximal and distal members to normally bias the constricting mechanism into the second state.

7. The method of claim 1 further comprising connecting a sleeve to the proximal and distal member such that the sleeve defines a passageway therethrough configured and dimensioned to receive the surgical instrument.

8. The method of claim 7, wherein the step of connecting the sleeve to the proximal and distal members includes orienting the sleeve such that, subsequent to insertion of the surgical instrument into the constricting mechanism, the sleeve is forced into engagement with an outer surface of the surgical instrument during repositioning of the constricting mechanism from the first state into the second state so as to form a substantially fluid-tight seal between the constricting mechanism and the surgical instrument.

9. The method of claim 1 further comprising associating at least one seal member with at least one of the proximal member and the distal member that is adapted to form a substantially fluid tight seal with the surgical instrument upon insertion of the surgical instrument into the constricting mechanism.

10. The method of claim 1, wherein the step of positioning the plurality of rods between the proximal and distal members includes interleaving the plurality of rods with each other such that the plurality of rods collectively define an aperture extending through the constriction mechanism for receipt of the surgical instrument.

11. The method of claim 10, wherein the step of positioning the plurality of rods between the proximal and distal members includes interleaving the plurality of rods such that one of the opposing ends of each rod is positioned distally of an adjacent rod in contact therewith, and the other of the opposing ends of each rod is positioned proximally of an adjacent rod in contact therewith.

12. The method of claim 10, wherein the step of positioning the rods between the proximal and distal members includes interleaving the plurality of rods such that the aperture extending through the constricting mechanism defines a first transverse dimension when the constricting mechanism is in the first state and a second, smaller transverse dimension when the constricting mechanism is in the second state.

13. The method of claim 1, wherein the step of positioning the plurality of rods between the proximal and distal members includes positioning the plurality of first pins within bores included in each of the plurality of rods, and positioning the plurality of second pins within slots included in each the plurality of rods such that relative rotation between the proximal and distal members causes the plurality of rods to pivot about the plurality of first pins as the plurality of second pins traverse the slots.

14. The method of claim 1, wherein the step of positioning the plurality of rods between the proximal and distal members includes orienting the first plurality of pins and the second plurality of pins such that stem portions of the pins pass through the plurality of rods, and head portions of the pins, which each define a transverse dimension greater than a transverse dimension defined by the corresponding stem portion, are positioned adjacent an outer surface of the plurality of rods.

15. The method of claim 14, wherein the step of providing the plurality of rods includes providing the plurality of rods such that each bore and each slot defines a substantially identical transverse dimension greater than the transverse dimension defined by the stem portion of each pin but less than the transverse dimension defined by the head portion of each pin such that the pins are securely engageable with the plurality of rods.

16. The method of claim 15, wherein the step of positioning the plurality of rods between the proximal and distal members includes positioning the plurality of first pins within the bores of each of the plurality of rods and positioning the plurality of second pins within the slots of each the plurality of rods such that relative rotation between the proximal and distal members causes the plurality of rods to pivot about the plurality of first pins as the plurality of second pins traverse the slots.

* * * * *